United States Patent [19]

Wyburn-Mason

[11] 4,073,922
[45] Feb. 14, 1978

[54] TREATMENT OF RHEUMATOID ARTHRITIS AND RELATED DISEASES

[75] Inventor: Roger Wyburn-Mason, Richmond Hill, England

[73] Assignee: John R. A. Simoons, Summit, N.J.

[21] Appl. No.: 700,914

[22] Filed: June 29, 1976

[30] Foreign Application Priority Data

Jan. 1, 1976 Japan .................................. 51-684

[51] Int. Cl.² .......................................... A61K 31/415
[52] U.S. Cl. ................................................ 424/273 R
[58] Field of Search ......................................... 424/273

[56] References Cited
U.S. PATENT DOCUMENTS 3,657,445  4/1972  Buctel et al. ........................ 424/273

OTHER PUBLICATIONS

The Medical Letter vol. 17, No. 19 (Sept. 12, 1975).
Journal of Tropical Medicine & Hygiene (vol. 75), March, 1972.

Primary Examiner—Stanley J. Friedman
Attorney, Agent, or Firm—Richard T. Laughlin

[57] ABSTRACT

It is believed that rheumatoid arthritis and related collagen and auto-immune diseases are an infection and that various species of free-living (limax) amoebae are the aetiological agent of these diseases. It has been discovered that clotrimazole [bis-phenyl (2-chlorphenyl)-1-imidazolyl-methane] and related compounds, antimycotic drugs with anti-protozoal activity, are effective for the treatment of rheumatoid arthritis and other collagen and auto-immune (rheumatoid) diseases.

5 Claims, No Drawings

TREATMENT OF RHEUMATOID ARTHRITIS AND RELATED DISEASES

BACKGROUND OF THE INVENTION

Men and other animals are continually exposed to infection and re-infection by various species and strains of free-living limax amoebae which can be detected in the faeces, nasopharynx and bronchi. In all parts of the world they form part of the environment. Experimentally in animals they induce changes like those of collagen and auto-immune diseases and are characterized by vasculitis, myosotis, hepatitis, pyelitis and splenomegaly. They can often be seen in the tissues of animals. Such animals show lymphadenopathy with an appearance like that of human Hodgkin's disease or a state like that of advanced malignant disease. These organisms may also be recovered from all the tissues of cases of collagen and auto-immune diseases and from human and many animal tumors and may also occur in the tissues of apparently healthy individuals. They cannot be identified in ordinary histological sections, but can be demonstrated by immunofluorescent methods.

The definite cause of rheumatoid arthritis is presently unknown. Rheumatoid arthritis is a crippling disease, characterized by the inflammation of several joints of the body, with swelling, pain and stiffness. Rheumatoid arthritis is a disorder that afflicts about fifteen million people in the Western World alone. Successful early treatment may avert the destructive, deforming phase of the disease. Therapy has been directed largely at non-specific suppression of inflammatory and immunologic processes. Asprin is the cornerstone of therapy for rheumatoid arthritis and can reduce synovial inflammation, improve function and reduce pain in a majority of patients in view of its analgesic action. Widespread interest in rheumatoid arthritis arose when Hench (1949) introduced the use of cortisone in treatment. Chemical compounds which have been commonly used in treating rheumatoid arthritis are corticosteroids, gold salts, antimalarial drugs, immunosuppressive agents and a whole range of so-called non-steroidal drugs, e.g. indomethacin, phenylbutazones, anthranilic acid, benzathiazine derivatives, phenylacetic acid (Ibuprofen), propionic acid (Naproxen) and D-penicillamine. Most of these drugs bring temporary relief to the arthritic patient but present the danger of side effects and the physician has to balance the potential benefit against the risks. However, arthritis reoccurs following withdrawal of such chemical treatment. For many years rheumatoid arthritis was considered to be an infection (Hollander et al., 1960; Robinson, 1967), but with the advent of the concept of auto-immunity this idea lost favor. Such a view has recently been revived (Lancet, 1970, 2, 303) and is supported by many observations. It is highly likely that the limax amoebae, found in all the collagen and auto-immune diseases, may well be the aetiological agent of these conditions and that anti-protozoal drugs may help by their action on these organisms.

The use of clotrimazole as an anti-fungal agent is known. Clotrimazole and related compounds for use as antimycotics is disclosed in U.S. Pat. No. 3,657,445 issued Apr. 18, 1972, to Buchel, et al. The use of clotrimazole is also described in the Sept. 12, 1975 issue (volume 17, No. 19) pages 77 to 78 of The Medical Letter published by The Medical Letter, Inc., 56 Harrison St., New Rochelle, N.Y. It has also been suggested to use nitroimidazole in the treatment of rheumatoid arthritis in the Journal of Tropical Medicine and Hygiene (vol 75) pages 64 to 66, Mar. 1972. It is believed that the nitro group in the imidazole ring is related to metronidiazole which is not effective in the treatment of rheumatoid arthritis. It is believed that the use of anti-fungal agents with anti-protozoal activity in the successful treatment of rheumatoid arthritis was not known prior to my discovery. Dehydrocholic acid has found use as a bile substitute.

DESCRIPTION OF THE INVENTION

It has been found that chemical compounds which have anti-protozoal activity are effective when administered internally for treating rheumatoid arthritis and related collagen and auto-immune (rheumatoid) diseases. Of this group of compounds, clotrimazole [bisphenyl (2-chlorphenyl)-1-imidazolyl-methane] has proven most effective.

Various other anti-protozoal drugs were tried on the cases of rheumatoid disease or of various localized manifestations of this. The substances investigated were 4-aminoquinolines (chloroquine), hydroxychloroquine (plaquenil), amodiaquine (camoquin); copper sulphate; bile salts (dehydrocholine), which are effective in killing the trophozooites of many amoebae in the concentration found in the small intestine; and clotrimazole (canesten). All of these were actually shown experimentally to kill limax amoebae. In addition, other anti-protozoal drugs were also investigated. They included suramin, pentamidine, dehydro-emetine (DHE or mebadin), metronidiazole (flagyl), nitroimidazole (naxogin (Erba)), phanquone (entobex) and diloxanide (furamide).

The 4-aminoquinolines were given by mouth in a dose of 200 and 400 mg. daily, reduced after a month to 200 mg. twice weekly, care being taken to examine the eyes at intervals to guard against keratitis or macular changes. Copper salts were administered as 25 mg. of copper sulfate in aqua chloroformi by mouth three times daily. This may produce vomiting and/or diarrhea and the dose has to be decreased to 10 mg. three times daily. Only a small amount of the metal is absorbed, however, and no other side effects are observed even when taken over several months. Bile salts as dehydrocholine were given in a dose of 500–1000 mg. three times a day by mouth. They may produce mild colic. This may be prevented by simultaneous administration of a kaolin mixture. Pentamidine was at first given by intramuscular injection into the buttock in doses of 200 mg. daily for 10 days. The course was repeated twice with intervals of 7 days between. This substance is liable to produce local necrosis or abscess formation. Pentamidine can be given by mouth, but this absorption is uncertain. Moreoever, it may produce nausea, vomiting and diarrhea. However, many patients tolerate it by this route. Capsules containing 200 mg. were especially made and a dose of 200 mg. twice daily to 400 mg. three times daily by mouth were tried in various combinations. Suramin was given by intravenous injection of 500 mg. in 10 ml. of water and after this every 4 days 1 G was injected until 10 G had been given. The course was repeated once after 4 months. Dehydro-emetine (DHE) was given by intramuscular injection in doses of 60 mg. daily for 10 days and repeated after 7 days, or 60 mg. three times daily by mouth for 7–12 days, repeated after an interval of 10 days. Before commencing treatment E.C.G.'s were taken and repeated before each successive injection. Metronidiazole (flagyl) was given in doses of 400–600 mg. three times daily by mouth and nitroimidazole (naxogin) in doses of 75 mg. three times daily. Phanquone (entobex) was given in doses of 100 mg. twice daily by mouth for 7 days, repeated at intervals of a week. Diloxanide (furamide) was given in doses of 500 mg. three times daily for 10 days and repeated once.

The various substances tested above were tried on cases of rheumatoid arthritis of varying severity, systemic lupus erythematosus, dermatomyositis and other manifestations of collagen and auto-immune disease and observations made on the clinical condition, oedema, morning stiffness, E.S.R., plasma proteins, RF, ANF and organ-specific antibodies in the serum. No attempt at a double-blind trial was made as it became obvious, fairly early or even the day after commencing treatment, whether beneficial effect was obtained and, furthermore, symptomatic improvement is associated with improvement or disappearance of the abnormal blood changes, indicating that the drug was effective and improvement not due to suggestion. No beneficial effect was obtained from flagyl, naxogin, entobex, suramin or furamide in the doses used. However, Abd-Rabbo et al. (1972), using a derivative of nitro-imidazole (naxogin), BT 985 Merck A.G., which is active against amoebae, giardia and trichomonas, obtained beneficial effects in one case of systemic lupus erythematosus and nine of ten cases of rheumatoid disease. The drug was given in doses of 250 mg. daily for 14–39 days. In the follow-up period of 3–6 months no treatment was given and it was noted that the pain recurred, yet not to the same degree as before medication.

Clotrimazole is an antimycotic drug, synthesized by the Bayer Laboratories in Elberfeld, Germany, by M. Plempel et al., Deutsche Medizinische Wochenschrift, 1969, 94,1356), known as BAYb 5097, also known as canesten or lotrimin (Delbay U.S.A.). It is chemically bis-phenyl (2-chlorphenyl)-1-imidazolyl-methane and approved by the U.S. Food and Drug Administration only for topical treatment of tinea and Candida infections of the skin. It is available as a 1% solution or cream for external use. Clotrimazole has an in vitro activity and inhibits growth of most strains of the various dermatophytes that cause tinea pedis, tinea cruris and tinea corporis. It also inhibits the growth of some strains of gram-positive bacteria and against trichomonas species in high concentrations (PR Sawyer et al., Drugs, 9:424, 1975). Clotrimazole is also available in vaginal tablets in 100 mg. tablets and it is reported to be active against vaginal trichomoniasis (J. D. Schnell, Postgraduate Medical Journal 50, Suppl. 1:79, 1974).

Oral clotrimazole has been tried for treatment of disseminated fungal infections (P. D. Hoeprich and A. C. Huston, J. Inf. Fis. 132:133, August 1975). It was also tried to treat a case of pulmonary aspergillomata in a child by Evans, Watson and Matthews (British Medical J., 1971, 4,599–600). Clotrimazole was reported to be amoebistatic and amoebicidal in different concentrations against the free-living amoeba, Naegleria fowleri and other related species (Jamieson and Anderson, 1974).

The method of determining the anti-protozoal activity of drugs on limax amoebae was as described by Fulton, C. Methods in Cell Biology (edited by D. M. Prescott), p. 341, New York, 1070, and followed by Jamieson and Anderson in Lancet, 1974, 1, 261. All experiments were performed using 5-day old 5 ml. cultures of amoebae in the axenic medium "A" of Fulton. A standard inoculum of 100 c.mm. of differing concentrations of amoebae was added to each 1 ml. tube containing the dilutions of the compound to be tested (dissolved initially in dimethyl sulfoxide) or other drugs in the axenic medium. The tubes were incubated for 5 days at 37° C. and the final concentration per c.mm. was compared with the initial count to determine percentage kill.

It has now been found that rheumatoid arthritis can be effectively treated with clotrimazole. It is believed that related compounds having anti-protozoal activity would also be effective. Such compounds are described in U.S. Pat. No. 3,657,445 and are N-trityl-imidazoles and salts thereof of the formula:

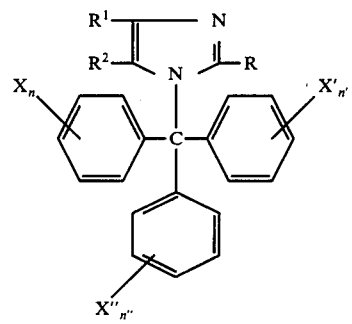

wherein
$R$, $R^1$ and $R^2$ are hydrogen, lower alkyl or phenyl, or $R^1$ and $R^2$ together form an anellated benzene ring,
$X$, $X'$ and $X''$ are alkyl of 1 to 12 carbon atoms or an electro-negative moiety, and
$n$, $n'$ and $n''$ are an integer from 0 to 2,
or pharmaceutically acceptable acid salts thereof. When $R$, $R^1$ or $R^2$ are alkyl moieties, those having 1 to 4 carbon atoms are preferred. When $X$, $X'$ or $X''$ is an alkyl moiety, it is preferred that such have 1 to 12 carbon atoms and such moieties having 1 to 4 carbon atoms are especially preferred. Electro-negative substituents which are particularly preferred are the halogens, i.e., fluorine, chlorine, bromine and iodine, $NO_2$, $CF_3$, $CN$, as well as S-lower alkyl and O-lower alkyl; it is preferred that the alkyl moieties have 1 to 4 carbon atoms. The term "alkyl" and "lower alkyl" comprises straight chain as well as branched chain alkyl moieties and also include those containing a double bond.

The salts of such N-trityl-imidazoles are the pharmaceutically acceptable non-toxic acid salts. Examples of suitable acids are the hydrohalic acids (hydrochloric being particularly preferred), phosphoric acid, mono- and bi-functional carboxylic acids, such as acetic acid, propionic acid, maleic acid, succinic acid, fumaric acid, tartaric acid, citric acid, salicylic acid, sorbic acid, lactic acid and 1,5-naphthalene-disulphonic acid. The hydrohalides, especially the hydrochlorides, lactates and salicylates are of particular value.

In a particularly preferred embodiment of the present invention, the N-trityl-imidazoles have the formula:

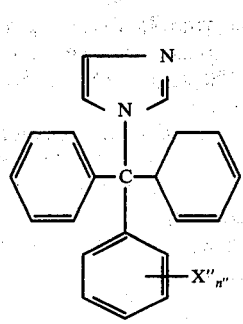

wherein X" is an electro-negative substituent such as fluorine, chlorine, bromine, iodine, $NO_2$, $CF_3$, CN, $SCH_3$, $OCH_3$ and $n''$ is 1.

The diagnosis of rheumatoid arthritis in 12 cases, reported by me during the Ninth International Congress of Chemotherapy held in London from July 13 – 18, 1975 (reported in Medical World News, Aug. 25, 1975), was consistent with the criteria of the American Rheumatism Association. The patients were hospitalized but not confined to bed. No other drugs were given and whatever drugs they took were discontinued, with the exception of corticosteroids, which were tapered off gradually. This resulted in an exacerbation of the symptoms, often severe. Serial investigations were carried out before and repeatedly during and after treatment. In seven cases RF and in four cases thyroid and gastric parietal cell auto-antibodies were present in the sera. Clotrimazole was administered orally in as near a dosage of 100 mg/kg per day as possible, taken in divided doses immediately after meals with milk. It can cause nausea, vomiting and diarrhea in certain patients. The former is controlled by an anti-emetic, which can follow the full dose of the drug to be taken. When it induced diarrhea, this could usually be prevented by a kaolin mixture.

Clotrimazole was administered to four males and eight females, their ages ranging from 47 to 77 years. Symtoms had been present for 2 months up to 23 years previously. In two cases the gastro-intestinal side effects of the drug were so severe as to prevent continuation of treatment for more than two to three days. All of the other ten cases showed a dramatically favorable response to treatment. This often began within 24 hours, when the oedema, pain, joint swelling, stiffness and restricted movements began to subside. The temperature settled. In one case, disappearance of all clinical evidence of active disease was complete in three days. In other cases it took two to four weeks for all evidence of active disease to disappear. In one case bilateral olecranon bursitis resolved completely in three weeks. It was found that administration of the drug had to be continued for eight to twelve weeks before it could be left off without a return of symptoms. Before treatment was commenced, most cases exhibited a rise in the ESR and seven of them some degree of anaemia and a reversal of the albumin-globulin ratio in the serum, while electrophoresis showed excess of alpha 2 globulin. In every case administration of the drug caused an increase in the ESR and a fall in the red blood cell count and hemoglobin content of the blood after about seven to ten days. This was sometimes associated with transient eosinophilia of up to 10 percent of 7,500 W.B.C. per cmm. In two cases at the time of the eosinophilia there developed slight transient painful lymphadenopathy and in three cases an itchy generalized erythematous rash lasting about one week. The ESR and blood count returned to normal in about six weeks. In four to six months the albumin-globulin ratio returned to normal and electrophoresis now showed no abnormality. All cases were followed up for 12 to 15 months and remained well. At the end of this time the RF and autoantibodies had disappeared from the blood. In those cases tolerating it, the drug thus completely reversed all the manifestations of activity in rheumatoid disease and its effects were so rapid in appearance as to resemble that of an antibiotic in cases of bacterial infection. Moreover, it was completely effective when all other antirheumatic drugs, including corticosteroids, had failed to control the disease. In some cases of first administration one may observe a transient exacerbation of the joint swelling and erythematous rash. These reactions resembled an Herzheimer reaction and suggest the drug was destroying an organism sensitive to the drug. The above account of the beneficial effects of clotrimazole on cases of rheumatoid disease was published in Modern Medicine, 1976, February 15th.

The treatments were carried out by administering clotrimazole in a dose of up to 100mg/kg/day whenever this dose can be tolerated by the patient. In several other studies I was able to obtain satisfactory results with daily doses of as low as 10–12 mg/kg/day. The optimal dose is believed to be approximately 25 mg/kg/day, which means that a patient of 60 kg should be given a dose of about 1.5 to 2.5 gram per day divided in 3 doses.

Similar results as obtained with clotrimazole were obtained with dehydrocholic acid. This latter compound was administered at the rate of 750 mg. three times a day with treatment for approximately three months to five months. A suitable treatment for an adult is three to five 250 mg. tablets three times a day.

It should be noted that the effects of anti-amoebic agents such as copper sulfate on rheumatoid disease may be only short-lived after cessation of their administration, suggesting that they do not kill the amoebae, but temporarily inhibit them, that is, they are amoebistatic not amoebicidal in the dosages it is possible to use in man. Clotrimazole, however, abolishes all manifestations of the disease (when administered in an optimum dose over a specified period of time), which do not return when the drug is stopped.

The therapeutically effective compound can be used either as such or in combination with pharmaceutically acceptable carriers. Suitable forms for administration in combination with various inert carriers are tablets, capsules, powders, aqueous suspensions, syrups and the like. The tablets and the like can be provided with an addition of saccharin or a similar additive. In the aforesaid case, the therapeutically active compound should be present in the total mixture at a concentration of about 0.5 to 90 percent by weight, i.e., in quantities which suffice to attain the range of dosage mentioned above. Tablets may also contain additives such as sodium citrate, calcium carbonate and dicalcium phosphate together with various additives such as starch and binders such as polyvinylpyrrolidine, gelatin and the like. It is further possible to add lubricants such as magnesium stearate, sodium lauryl-sulphate and talc for producing tablets.

EXAMPLE I

|  | Weight |  |
|---|---|---|
| Micronized clotrimazole powder | 5.0 | Kg |
| Cornstarch powder | 0.52 | Kg |
| Avicel (microcrystalline cellulose) PH 102 | 1.8 | Kg |
| Methocel 50 HG, 60 CPS | 100 | gm. |
| Purified water | q.s. |  |

The clotrimazole powder is mixed in a suitable blender with the other components and then the granulated mass is passed through an oscillator equipped with a 20-mesh screen. The granules are dried in an air circulating oven at 50° C. until a moisture content of less than 3% is reached. The granules are screened through a 20-mesh screen, lubricated with stearic acid 30 gm. and magnesium stearate 50 gm. The final mix is compressed into tablets of 750 mg. each, which contain 500 mg. of clotrimazole per tablet and can be used for oral administration Any departure from the foregoing description which conforms to the present invention is intended to be included within the scope of the claims.

What is claimed is:

1. A method for producing remission in patients suffering from active rheumatoid arthritis which comprises administering to such a patient a bis-phenyl (2-halophenyl)-1-imidazolyl-methane wherein the halo substituent is selected from the group consisting of chlorine, bromine and iodine.

2. The method of claim 1 wherein the daily dose amount is from about 1.5 to about 2.5 grams per day.

3. The method of claim 1, wherein the bis-phenyl (2-halophenyl)-1-imidazolyl-methane is clotrimazole.

4. The method of claim 1, wherein the bis-phenyl (2-halophenyl-1-imidazolyl-methane is clotrimazole and is administered orally in doses of approximately 100 mg. per kilogram of body weight per day.

5. The method of combating rheumatoid arthritis of claim 3, which comprises orally administering to the infected subject clotrimazole in a total daily dose amount of about 10 to 100 miligrams per kilogram of body weight.

* * * * *